United States Patent [19]

Shieh et al.

[11] 4,000,258
[45] Dec. 28, 1976

[54] LIQUID COMPOSITIONS OF *BACILLUS THURINGIENSIS*

[75] Inventors: Tsuong R. Shieh, Bannockburn; Martin H. Rogoff, Highland Park, both of Ill.

[73] Assignee: Sandoz, Inc., E. Hanover, N.J.

[22] Filed: Jan. 19, 1972

[21] Appl. No.: 219,147

[52] U.S. Cl. .................................................. 424/93
[51] Int. Cl.² ........................................ A01N 15/00
[58] Field of Search ..................................... 424/93

[56] References Cited

UNITED STATES PATENTS

| | | | |
|---|---|---|---|
| 3,087,865 | 4/1963 | Drake et al. | 424/93 |
| 3,271,243 | 9/1966 | Cords et al. | 424/93 |

FOREIGN PATENTS OR APPLICATIONS

| | | | |
|---|---|---|---|
| 1,004,327 | 9/1965 | United Kingdom | 424/93 |

*Primary Examiner*—V. D. Turner
*Attorney, Agent, or Firm*—Gerald D. Sharkin; Richard E. Vila

[57] ABSTRACT

Stable suspensions of *Bacillus thuringiensis* insecticide in a liquid selected from the group consisting of (a) alcohols having at least about 7 carbon atoms; (b) polyethylene glycols having a molecular weight of at least about 300; (c) polypropylene glycols having a molecular weight of at least about 180; (d) polyethylenepropylene glycols having a molecular weight of at least about 250; (e) ethoxylated alcohols having a molecular weight greater than about 120; and (f) propoxylated alcohols having a molecular weight greater than about 120.

4 Claims, No Drawings

LIQUID COMPOSITIONS OF BACILLUS THURINGIENSIS

DESCRIPTION OF THE INVENTION

*Bacillus thuringiensis*, a spore-forming microorganism with crystalline parasporal bodies, has been employed commercially as a microbial insecticide for the control of insects such as species of the order Lepidoptera. Common examples of Lepidoptera include the cabbage looper, armyworm, tobacco hornworm, tomato hornworm, alfalfa caterpillar, and the like. The larva of these insects, because of their feeding habits, are capable of causing extensive damage to the host plant.

*B. thuringiensis* and its use as an insect pathogen is described, inter alia, in C. L. Hannay and P. Fitz-James, "The Protein Crystals of *Bacillus thuringiensis* Berliner", *Can. J. Microb.*, I., 694–710, (1955); Louis W. Labaw, "The Structure of *Bacillus thuringiensis* Berliner Crystals", *J. Ultrastructure Research*, 10, 66–75, (1964); A. M. Heimpel, "A Critical Review of *Bacillus thuringiensis* Var. thuringiensis Berliner and Other Crystalliferous Bacteria", *Ann. Rev. Entomology*, 12, 287–322, (1967); and U.S. Pat. No. 3,073,749 and references cited therein. Formulations designed for *B. thuringiensis* are described in U.S. Pat. Nos. 3,271,243 and 3,113,066, while general pesticide formulations that may include *B. thuringiensis* as one alternate of a number of possible ingredients are described in U.S. Pat. Nos. 3,236,622 and 3,333,942.

*B. thuringiensis* insecticides are quite specific and are entirely harmless to non-susceptible orders of insects, animals and man. Because *B. thuringiensis* is harmless to man, treatment of the host plant can continue from the onset of an insect infestation until harvest of the crop, even though the crop is edible.

*B. thuringiensis*, a biological insecticide, may exhibit a loss of potency upon storage. While the exact mechanism that results in the loss of potency has not been unequivocally defined, it appears that potency loss is probably due to enzymatic and/or physiochemical denaturation processes. It has been recognized that the presence of water may hasten the deterioration of the insecticidal activity.

Dried, wettable *B. thuringiensis* products have been provided which may be characterized by a greater stability than aqueous concentrates which are also available. Since *B. thuringiensis* is applied in small concentrations per acre, it is most desirable to apply the insecticides in a water carrier so that an even distribution of the insecticide is achieved. If the *B. thuringiensis* insecticide is provided as a dry, wettable powder, it becomes necessary for the applicator to re-suspend the insecticide in the aqueous medium. Such operation requires additional field equipment and incurs the risk that the insecticide will not be uniformly distributed in the water carrier and that uneven application will occur.

In order to avoid the difficulties posed by a dry powder, commercial *B. thuringiensis* concentrates in an aqueous medium are available. With such concentrates, however, careful handling, use of anti-oxidants and the like are required to minimize the loss of activity in such formulations.

It is one object of this invention to provide a stable concentrated *B. thuringiensis* insecticide.

It is still a further object of this invention to provide a concentrated stable liquid *B. thuringiensis* insecticide that readily may be diluted with water.

In accordance with this invention there is provided a stable pesticide concentrate which comprises a suspension containing *B. thuringiensis* solids and having a potency of at least 1 billion International Units per quart, said suspension containing at least about 15% solids having a mesh size of less than about 100 mesh in a liquid carrier selected from the group consisting of (a) monohydric alcohols having at least about 7 carbon atoms; (b) polyethylene glycols having a molecular weight of at least about 300; (c) polypropylene glycols having a molecular weight of at least about 180; (d) polyethylene-propylene glycols having a molecular weight of at least about 250; (e) ethoxylated alcohols having a molecular weight greater than about 120; and (f) propoxylated alcohols having a molecular weight greater than about 120.

It has been discovered that use of the above defined liquids as carriers provides *B. thuringiensis* suspensions which retain insecticidal potency well. Even though suspensions of *B. thuringiensis* in lower molecular weight alcohols (e.g., methonal or butanol) or in lower molecular weight glycols (e.g., dipropylene glycol, tripropylene glycol, or ethylene glycol) are not effective to provide *B. thuringiensis* concentrates that retain their potencies, it has been determined that the alcohols and glycols within the recited ranges do provide stable concentrates.

*B. thuringiensis* solids will include spores and parasporal crystal bodies produced by the microorganism. In addition, the product normally will contain cell solids as well as unused solids from the nutrient medium since it generally is not economical to remove these materials. The potency of the active ingredients in the *B. thuringiensis* solids will vary depending on the particular strain of microorganism employed, the medium employed, the culture time and conditions, and the method of recovery of the solids. Generally, however, the potency will vary between about 2 to about 20 billion International Units (BIU) and often from about 4 to about 16 BIU per pound of solids. An International Unit is a standard means of measuring the potency of *B. thuringiensis* and is described in detail in the literature.

The culturing of *B. thuringiensis* is well known in the art (see, e.g., U.S. Pat. No. 3,073,749), does not form part of this invention, and will not be described herein in detail.

The *B. thuringiensis* solids employed in the practice of this invention will preferably have a water content of less than about 10%. Such water content readily may be achieved employing known drying techniques. For instance, the final whole culture may be spray dried at temperatures of, for example, about 25° C. Alternately, the *B. thuringiensis* culture from the fermentor may be freeze dried, drum dried, or the like. The method employed to dry the *B. thuringiensis* insecticide is not critical to the practice of this invention.

The *B. thuringiensis* solids undergo some swelling when suspended in the liquids of this invention. The *B. thuringiensis* solids employed in this invention when in suspension substantially all pass through 100 mesh (Tyler mesh size) so that the suspensions can be applied employing standard agricultural nozzles. Desirably the suspensions of this invention pass through 200 mesh. *B. thuringiensis* solids obtained by drying techniques such as spray drying generally provide suspensions that pass through 200 mesh directly, although solids obtained by drying techniques such as drum drying may require comminuting to provide small enough particles for the suspension.

At least about 15% solids by weight are needed to minimize settling. While B. thuringiensis solids can be only the solids present in the suspensions of this invention, it may be desirable for some applications to employ B. thuringiensis at concentrations less than 15% solids. In some cases, as little as 4% B. thuringiensis solids may be employed. In such cases, dry solids other than B. thuringiensis may be employed to provide the requisite solids concentrations. Such other solids may be any inert finely divided (i.e., −100 mesh, preferably −200 mesh) solid such as talc, clays such as bentonite, vegetable meals such as soy flour, or the like. Such solids desirably have a density that approximates the density of B. thuringiensis solids (about 1.2 gm/cc) and, therefore, solids having a density of from about 1 to about 2 gm/cc are preferred. Generally, the suspension will contain from about 15% to about 40% by weight solids.

From a practical standpoint, the concentrated suspensions of this invention will have a potency of at least about 1 BIU per quart. Suspensions frequently will have potencies of from about 1 to about 20 BIU per quart and most often from about 4 to about 16 BIU per quart.

The media for the suspension is a liquid at 45° F. and preferably has a viscosity of more than 200 centistokes at 45° F. Monohydric alcohols having at least 7 carbon atoms constitute one class of liquids useful in this invention. Representative alcohols include heptanol, diisopropyl carbinol, 4 methyl -1-hexanol, 2- ethyl -1- hexanol, and lauryl alcohol. The alcohol may be a branched chain alcohol and the OH group may be at any position in the chain. Generally, the alcohol will have from 7 to 12 carbon atoms.

The liquid polyethylene glycols, polypropylene glycols and mixed polyethylenepropylene glycols useful in the practice of this invention are well known materials formed, for example, from ethylene glycol, ethylene oxide, propylene glycol, propylene oxide, or mixtures of ethylene glycol and propylene glycol or ethylene oxide and propylene oxide to provide polyether glycols. Polyethylene glycols useful for this invention have a molecular weight of at least about 300, and preferably from about 400 to about 600. Polypropylene glycols remain liquid through a much greater molecular weight range than polyethylene glycols. Any liquid polypropylene glycol having a molecular weight greater than about 180 may be used in this invention. Polypropylene glycols having a molecular weight from about 400 to about 4,000 are particularly preferred. In much the same vein, any liquid polyethylenepropylene glycol having a molecular weight above about 250 may be employed in this invention, while polyethylenepropylene glycols having a molecular weight from about 400 to about 2,000 are preferred.

Ethoxylated and propoxylated alcohols are ethers formed by the reaction of ethylene oxide or propylene oxide with an alcohol. Representative ethoxylated alcohols include ethoxybutanol, ethoxyhexanol, and ethoxyoctanol. Representative examples of propoxylated alcohols include propoxybutanol, propoxyhexanol, and propoxyoctanol. The ethoxylated alcohols and propoxylated alcohols useful in this invention have a molecular weight greater than about 120.

Simple mixing of the ingredients is generally sufficient to provide the suspension of this invention. At times it may be advantageous to form a slurry of solids with the liquid carrier and then dilute that slurry to the desired concentration.

The effect of the water content of B. thuringiensis formulations, especially when the formulation is exposed to prolonged storage at elevated temperatures, has not been unequivocally determined. The water content of the formulation of this invention will not exceed 35% (prior to dilution just before application), preferably will not exceed 15%, and still more preferably will be less than 5% by weight of the formulation.

At the time of application, the concentrates of this invention may be admixed with water to provide the desired potency for application. B. thuringiensis generally is applied at the rate of from about 0.5 to about 20 BIU per acre and often from about 1 to about 16 BIU per acre. Most often application rates range from about 1.5 to about 8 BIU per acre. The amount of water diluent employed is obviously a matter of choice with the applicator. Most often from about 1.0 to about 10 gallons per acre are used for aerial application, and about 10 to 100 gallons per acre for ground application.

The following examples are included herein for illustrative purposes only and are in no way intended to limit the scope of this invention.

In the following examples the potency measurements (U/ml) are the reciprocal of the dilution required to provide an $LD_{50}$ in 5 days on 3rd instar cabbage looper (*Trichoplusia ni*) larvae. Insecticide solution and the larval diet were mixed in equal quantities in these tests. The bioassays followed generally that described by Dulmage et al., "A Proposed Standardized Bioassay for Formulations of *Bacillus Thuringiensis* Based on the International Unit", *Journal of Invertebrate Pathology*, 18, 240–245 (1971).

EXAMPLE I

Ten ml of various molecular weight of glycols and alcohols containing 5% by weight of a spray dried preparation of B. thuringiensis were heated at 75° C. for 50 minutes. The spore count of the suspensions and their potency against the cabbage looper were thereafter determined. The results are shown in Table 1.

Table 1

| Medium | Spore Count ($\times 10^9$/ml) | Potency |
| --- | --- | --- |
| Methanol | 0.4 | Nil |
| Butanol | 2.6 | 1400 |
| Ethylene glycol | 0.65 | Nil |
| Diethylene glycol | 0.82 | Nil |
| Triethylene glycol | 1.30 | Nil |
| Propylene glycol | 0.68 | Nil |
| Water | 3.4 | 4000 |
| Water (not heated) | 3.7 | 3600 |

The results of the above tests clearly demonstrate that the lower molecular weight glycols and alcohols actually increase degradation of the insecticide as compared to the water controls.

EXAMPLE II

The test of Example 1 was repeated employing octanol as the medium.

Table 2

| Medium | Spore Count ($\times 10^9$/ml) | Potency |
|---|---|---|
| Octanol | 3.8 | 3800 |

The results shown in Table 2 demonstrate that, in contrast to the lower molecular weight alcohols of Example I, the higher molecular weight alcohols do not accelerate degradation of the insecticide.

EXAMPLE III

The test of Example I was repeated employing ethoxylated butanol (ethylene glycol monobutyl ether).

Table 3

| Medium | Spore Count ($\times 10^9$/ml) | Potency |
|---|---|---|
| Ethoxylated butanol | 3.8 | 4700 |

EXAMPLE IV

Twenty-eight gm of spray dried *B. thuringiensis* concentrate were blended into 180 ml of solutions of non-aqueous liquids containing 25% xylene and 4% isooctyl phenyl polyoxyethanol (Triton X-100) surfactant. Ten ml aliquots were placed in sampling tubes and were heated in a water bath at 75° C. for 8 hours. Spore counts and bioassays were then conducted. The results are shown in Table 4.

Table 4

| Medium | Spore Count ($\times 10^{10}$/ml) | Potency |
|---|---|---|
| Controls | | |
| Water | < 0.003 | 2800 |
| Water (not heated) | 1.3 | & 9600–15,000 |
| Test Media | | |
| Octanol | 1.2 | & 9800 |
| Polyethylene glycol (mw 200) | 0.19 | Nil |
| Polyethylene glycol (mw 400) | 0.93 | 9600 |
| Dipropylene glycol (mw 134) | 0.3 | 5200 |
| Polypropylene glycol (mw 192) | 0.96 | 8400 |

The results of Table 4 demonstrate that the octanol and higher molecular weight polyethylene glycols and higher molecular weight polypropylene glycols protect the potency of the preparation, whereas their lower molecular weight counterparts do not.

EXAMPLE V

Samples were prepared as in Example III except that the xylene and the surfactant were omitted from the suspensions. The samples were heated at 70° C. for 14 days and the spore count and potency thereafter measured. The results are shown in Table 5 below.

Table 5

| Medium | Spore/ml | Potency |
|---|---|---|
| Controls | | |
| Water | < 5.0 $\times 10^4$ | Nil |
| Water (no storage) | 1.3 $\times 10^{10}$ | & 9600–15,000 |
| Test Media | | |
| Octanol | 6.1 $\times 10^8$ | & 10,000 |
| Polyethylene glycol (mw 200) | < 5.0 $\times 10^4$ | Nil |
| Polyethylene glycol (mw 400) | < 5.0 $\times 10^4$ | 3,300 |
| Dipropylene glycol | 1.1 $\times 10^8$ | Nil |
| Polypropylene glycol (mw 192) | < 1.0 $\times 10^7$ | 2,600 |

While the data of Table 5 indicate that spore counts generally decreased, the potency of the insecticide in octanol and the higher molecular weight polyethylene glycols and polypropylene glycols were substantially greater than the water control which had no remaining potency at the end of the test period.

EXAMPLE VI

For this test the liquids identified in Table 5 (containing 30% xylene) were employed. Forty grams of spray dried *B. thuringiensis* concentrate was blended with sufficient amount of each liquid to bring the volume to 100 ml. The samples were stored at 50° C. for 3 months and the potencies were thereafter measured. The results are shown in Table 6.

Table 6

| Medium | Potency |
|---|---|
| Control | |
| Water | Nil |
| Water (no storage) | 8,000 |
| Test Media | |
| Octanol | 7,600 |
| Polyethylene glycol (mw 200) | Nil |
| Polyethylene glycol (mw 400) | 7,600 |
| Dipropylene glycol | 3,000 |
| Polypropylene glycol (mw 192) | 5,200 |

Once again the data of Table 6 contrast the liquids of this invention with their lower molecular weight counterparts.

It is generally (though not always) desirable to employ a surfactant in the non-aqueous suspension of this invention in order to provide a suspension with reduced tendency to settle. Surfactants are particularly useful with liquids that are not water miscible. The surfactant may be an anionic, non-ionic or cationic surfactant and often is employed in amounts from about 0.1 to about 10% by weight. Each type is, of course, well known in the art. Representative surfactants are described inter alia, in U.S. Pat. No. 3,271,243.

The bacterial insecticide concentrate compositions of the present invention also may, if desired, contain various supplemental ingredients. Thus, for instance, there may be added thereto small proportions of sticking or adhesive agents such as glue or rosin to increase the property of adherence of the compositions, after dilution with water, to the plant surfaces or the like to which said diluted compositions are applied. Again, the concentrate compositions may have added thereto small proportions, of the order of 1 to 2%, of odorous or odor masking materials of various types, an illustrative example of which is naphthalene. Other possible additions include anti-oxidants, anti-bacterial agents (e.g., xylene), ultraviolet screening agents and the like. Furthermore, other insecticidal materials may be incorporated into the concentrate compositions to obtain multipurpose effects.

Since modifications of this invention will be apparent to those skilled in the art, it is intended that the invention be limited only by the scope of the appended claims.

We claim:

1. A liquid insecticide suspension consisting essentially of *B. thuringiensis* solids and a liquid monohydric alcohol having 7 to 12 carbon atoms as carrier therefor; said suspension having a potency of at least 1 billion International Units per quart and containing about 15% to about 40% solids having a mesh size of less than about 100 mesh.

2. A liquid insecticide suspension consisting essentially of *B. thuringiensis* solids and a liquid polyethylene glycol having a molecular weight of at least about 300 as carrier therefor; said suspension having a potency of at least 1 billion International Units per quart and containing about 15% to about 40% solids having a mesh size of less than about 100 mesh.

3. A liquid insecticide suspension consisting essentially of *B. thuringiensis* solids and a liquid polypropylene glycol having a molecular weight of at least about 180 as carrier therefor; said suspension having a potency of at least 1 billion International Units per quart and containing about 15% to about 40% solids having a mesh size of less than about 100 mesh.

4. A liquid insecticide suspension consisting essentially of *B. thuringiensis* solids and a liquid polyethylene propylene glycol having a molecular weight of at least about 250 as carrier therefor; said suspension having a potency of at least 1 billion International Units per quart and containing about 15% to about 40% solids having a mesh size of less than about 100 mesh.

* * * * *